United States Patent [19]

Wilmore

[11] Patent Number: 5,292,722
[45] Date of Patent: Mar. 8, 1994

[54] INTRAVENOUS SOLUTION THAT DIMINISHES BODY PROTEIN LOSS

[75] Inventor: Douglas Wilmore, Brookline, Mass.

[73] Assignee: Brigham and Women's Hospital, Boston, Mass.

[21] Appl. No.: 971,623

[22] Filed: Nov. 6, 1992

[51] Int. Cl.⁵ .................. A61K 31/195; A61K 31/70
[52] U.S. Cl. ......................... 514/23; 514/867; 514/909; 514/910; 514/563; 426/804; 426/810
[58] Field of Search ............ 426/804, 810; 514/23, 514/867, 909, 910, 563

[56] References Cited

U.S. PATENT DOCUMENTS

| | | | |
|---|---|---|---|
| 1,909,591 | 5/1933 | Nevin | 604/56 |
| 2,283,817 | 5/1942 | Martin et al. | 514/255 |
| 2,662,046 | 12/1953 | Howe | 514/400 |
| 2,868,693 | 1/1959 | Shive et al. | 514/561 |
| 3,195,778 | 7/1965 | Coates | 222/80 |
| 3,217,711 | 11/1965 | Pecina et al. | 604/81 |
| 3,574,857 | 4/1971 | Cevallos | 514/561 |
| 3,701,666 | 10/1972 | Wimitz | 426/311 |
| 3,793,450 | 2/1974 | Schnell | 424/195 |
| 3,832,465 | 8/1974 | Ghadimi | 514/19 |
| 3,920,838 | 11/1975 | Flatt et al. | 514/400 |
| 3,950,529 | 4/1976 | Fischer et al. | 514/400 |
| 3,982,534 | 9/1976 | Buckman | 604/81 |
| 3,988,466 | 10/1976 | Takagi et al. | 514/561 |
| 4,200,095 | 4/1980 | Reti | 604/81 |
| 4,265,240 | 5/1981 | Jenkins | 604/82 |
| 4,334,535 | 6/1982 | Wilson et al. | 604/82 |
| 4,396,383 | 8/1983 | Hart | 604/56 |
| 4,439,448 | 3/1984 | Munakata et al. | 424/309 |
| 4,857,555 | 8/1989 | Smith et al. | 514/563 |
| 5,039,704 | 8/1991 | Smith et al. | 514/563 |

FOREIGN PATENT DOCUMENTS

| | | |
|---|---|---|
| 1285491 | 7/1991 | Canada . |
| 052296 | 10/1981 | European Pat. Off. . |
| 059694 | 9/1982 | European Pat. Off. . |
| 087750 | 3/1983 | European Pat. Off. . |
| 3206784 | 2/1982 | Fed. Rep. of Germany . |
| 56-131554 | 10/1981 | Japan . |
| 59-130253 | 7/1984 | Japan . |
| 1125820 | 9/1968 | United Kingdom . |

OTHER PUBLICATIONS

Alverdy, John C. et al., "The Effect of Route of Nutrient Administration on the Secretory Immune System", *Current Surgery*, pp. 10-13 (Jan./Feb. 1985).

Alverdy, John C. et al., "The Effect of Parenteral Nutrition on Gastrointestinal Immunity-The Importance of Enteral Stimulation", *Ann. Surg.* 202(6):681-684 (Dec. 1985).

Amberger, I. et al., "The Potential Parenteral Application of the Peptide L-Alanyl-L-Glutamine as a Nitrogen Source in Severe Catabolic States", *Hoppe-Seyler's Z. Physiol. Chem.* 364:1253-1254 (1983).

Andrassy, Richard et al., "Symposium: Nutrition for AIDS Patients", *Contemp. Surg.* 35:53-79 (Nov. 1989).

Aoki, Thomas T. et al., "Leucine Meal Increases Glutamine and Total Nitrogen Release from Forearm Muscle", *J. Clin. Invest.* 68:1522-1528 (Dec. 1981).

Askanazi, J. et al., "Muscle and Plasma Amino Acids after Injury", *Ann. Surg.* 191(4):465-472 (Apr. 1980).

Askanazi, J. et al., "Muscle and Plasma Amino Acids Following Injury-Influence of Intercurrent Infection", *Ann. Surg.* 192(1):78-85 (Jul. 1980).

Baskerville, A. et al., "Pathological Features of Glutaminase Toxicity", *Br. J. exp. Path.* 61:132-138 (1980).

Bergner, H. et al., "Influence of the Glutamic Acid (List continued on next page.)

*Primary Examiner*—Ronald W. Griffin
*Attorney, Agent, or Firm*—Sterne, Kessler, Goldstein & Fox

[57] ABSTRACT

The present invention provides compositions and methods of decreasing the nitrogen loss in a mammal which is normally associated with the administration of isocaloric solutions. Specifically, the present invention provides compositions comprising from about 4% to 10% dextrose and from about ½% to 2% glutamine. Such compositions, when administered to a mammal, reduces dehydration and nitrogen loss to approximately 25% of that found when no solution is administered.

6 Claims, No Drawings

OTHER PUBLICATIONS

Content of the Diet on the Catabolic Rate of Labeled Glutamic Acid in Rats", *Biol. Abstr.* 79(10): Abstract 88557 (1985).

Bergström, J. et al., "Intracellular Free Amino Acid Concentration in Human Muscle Tissue", *J. App. Physiol.* 36(6):693–697 (Jun. 1974).

Cersosimo, E. et al., "Role of Glutamine in Adaptations in Nitrogen Metabolism during Fasting", *Am. J. Physiol.* 250:E622–E628 (1986).

Cheney, Carrie L. et al., "Body Composition Changes in Marrow Transplant Recipients Receiving Total Parenteral Nutrition", *Cancer* 59:1515–1519 (1987).

Chipponi, Jacques X. et al., "Deficiencies of Essential and Conditionally Essential Nutrients", *Am. J. Clin. Nutr.* 35:1112–1116 (May 1982).

Clowes, George H. A. et al., "Effects of Parenteral Alimentation on Amino Acid Metabolism in Septic Patients", *Surgery* 88(4):531–543 (Oct. 1980).

Cunningham, Beth Ann et al., "Nutritional Considerations during Marrow Transplantation", *Nursing Clinics of North America* 18(3):585–596 (Sep. 1983).

Derr, Robert F. et al., "Total Parenteral Nutrition: Improved Formula for Healing Rat Jejunal Anastomoses" *Nutrition Reports International* 23(4):749–753 (Apr. 1981).

Durschlag, Roberta P. et al., "Regulation of Glutamine Production by Skeletal Muscle Cells in Culture", *Am. J. Physiol.* 248:C442–C448 (1985).

Durschlag, Roberta P. et al., "Glutamine Production by Skeletal Muscle in Tissue Culture", *Federation Proceedings* 42:996 [Entry 4126] (1983).

Elia, Marinos et al., "Alanine and Glutamine Release from the Human Forearm: Effects of Glucose Administration", *Chem. Abs.* 103:Abstr. 102688t (1985).

Fürst, P. et al., "Influence of Amino Acid Supply on Nitrogen and Amino Acid Metabolism in Severe Trauma", *Act Chir. Scand. Suppl.* 494:136–138 (1979).

Gamble, James L., "Physiological Information Gained from Studies on the Life Raft Ration", *Harvey Lectures* 42:247–273 (1946–1947).

Hambleton, P. et al., "Clinical Biochemical Aspects of Glutaminase Toxicity in Rabbits and Rhesus Monkeys", *Br. J. exp. Path.* 61:208–216 (1980).

Hammarqvist, Folke et al., "Addition of Giutamine to Total Parenteral Nutrition after Elective Abdominal Surgery Spares Free Glutamine in Muscle, Counteracts the Fall in Muscle Protein Synthesis, and Improves Nitrogen Balance", *Ann. Surg.* 209(4):455–461 (Apr. 1989).

Hanson, Peter John et al., "Metabolism and Transport of Glutamine and Glucose in Vascularly Perfused Small Intestine Rat", *Biochem. J.* 166:509–519 (1977).

Harada, M. et al., "Changes in Biological Elements in Mouse Stress Ulcer and Effects of Drugs", *Folia Pharmacol. JPN* 69(6):322P (1973).

Heath, D. F. et al., "The Effects of the Stress Caused by Experimental Procedures on Alanine, Aspartate, Glutamate and Glutamine in Rat Liver", *Biochem. J.* 125:765–771 (1971).

Hong, Chang-Zern et al., "Metabolic Effects of Exhaustive Training of Athletes", *Biol. Abstr.* 78(9):Abstr. 70581 (1984).

Hughes, C. A. et al., "Speed of Change in Pancreatic Mass and in Intestinal Bacteriology of Parenterally Fed Rats", *Clinical Science* 59:329–336 (1980).

Ivanova, I. A. et al., "Comparative Study of Some Drugs on Different Models of Brain Hypoxia", *Biol. Abstr.* 80(4):Abstr. 34601 (1985).

Johnson, Daniel J. et al., "Branched Chain Amino Acid Uptake and Muscle Free Amino Acid Concentrations Predict Postoperative Muscle Nitrogen Balance", *Ann. Surg.* 204(5):513–523 (Nov. 1986).

Johnson, Daniel J. et al., "Glutamine Infusion Supports Plasma Amino Acid Metabolism during Simulated Stress", *Curr. Surg.* 43:31–34 (Jan.–Feb. 1986).

Johnson, Leonard R., "Regulation of Gastrointestinal Growth", chapter 10 of *Physiology of the Gastrointestinal Tract*, 2nd ed. (L. R. Johnson, ed.), Raven Press, New York (1987).

Johnson, Leonard R. et al., "Structural and Hormonal Alterations in the Gastrointestinal Tract of Parenterally Fed Rats", *Gastroenterology* 68(5):1177–1183 (1975).

Johnson, Leonard R. et al., "Effect of Long-Term Parenteral Feeding on Pancreatic Secretion and Serum Secretin", *Amer. J. Physiol.* 233:E524–E529 (1977).

Kapadia, C. Raja et al., "Maintenance of Skeletal Muscle Intracellular Glutamine during Standard Surgical Trauma", *J. of Parenteral and Enteral Nutrition* 9(5):583–589 (1985).

Kapadia, C. Raja et al., "Alterations in Glutamine Me- (List continued on next page.)

OTHER PUBLICATIONS tabolism in Response to Operative Stress and Food Deprivation", *Surgical Forum* 33:19-21 (1982).

Korein, Julius, "Treatment Questioned in Familial Spasmodic Torticollis", *Neurology* 27:899-900 (Sep. 1977).

Korein, Julius, "Oral L-Glutamine Well Tolerated", *The New England Journal of Medicine* 301:1066 (Nov. 8, 1979).

Lenssen, Polly et al., "Parenteral Nutrition in Marrow Transplant Recipients after Discharge from the Hospital", *Exp. Hematol.* 11(10):974-981 (Nov. 1983).

Lenssen, Polly et al., "Intravenous Branched Chain Amino Acid Trial in Marrow Transplant Recipients", *J. of Parenteral and Enteral Nutrition* 11(2):112-118 (Mar.-/Apr. 1987).

Levine, Gary M. et al., "Small-Bowel Resection-Oral Intake Is the Stimulus for Hyperplasia", *Digestive Diseases* 21(7):542-546 (Jul. 1976).

Levine, Gary M. et al., "Role of Oral Intake in Maintenance of Gut Mass and Disaccharide Activity", *Gastroenterology* 67(5):975-982 (Nov. 1974).

Levintow, Leon et al., "The Role of Glutamine in Protein Biosynthesis in Tissue Culture", *J. Biol. Chem.* 227:929-941 (1957).

Longton, R. W. et al., "Initiation of Gingival Lesions during Amino Acid Stress", *BioReviews* 10:183 [Entry 498] (1973).

MacLennan, Peter A. et al., "A Positive Relationship between Protein Synthetic Rate and Intracellular Glutamine Concentration in Perfused Rat Skeletal Muscle", *FEBS* 215(1):187-191 (May 1987).

MacLennan, Peter A. et al., "Inhibition of Protein Breakdown by Glutamine in Perfused Rat Skeletal Muscle", FEBS 237:133-136 (Sep. 1988).

Marliss, E. B. et al., "Muscle and Splanchnic Glutamine and Glutamate Metabolism in Postabsorptive and Starved Man", *J. Clin. Invest.* 50:814-817 (1971).

Menzies, Ian S., "Absorption of Intact Oligosaccharide in Health and Disease", *Biochem. Soc. Trans.* 550(2):1042-1047 (1974).

Milakofsky, Louis et al., "Rat Plasma Levels of Amino Acids and Related Compounds during Stress", *Life Sciences* 36:753-761 (1985).

Moyer, Mary Pat et al., "Effects of Gastrin, Glutamine, and Somatostatin on the In Vitro Growth of Normal and Malignant Human Gastric Mucosal Cells", *Chem. Abstr.* 104: Abstr. 219523X (1986).

Muhlbacher, Ferdinand et al., "Effects of Glucocorticoids on Glutamine Metabolism in Skeletal Muscle", *Am. J. Physiol.* 247:E75-E83 (1984).

Newsholme, E. A. et al., "The Role of High Rates of Glycolysis and Glutamine Utilization in Rapidly Dividing Cells", *Bioscience Reports* 5:393-400 (1985).

O'Dwyer, S. T. et al., "5-Fluorouracil Toxicity on Small Intestinal Mucosa but not White Blood Cells is Decreased by Glutamine", *Clinical Research* 35(3):369A (1987).

Ohta, H. et al., "Effect of L-Glutamate, Injected into the Posterior Hypothalamus, on Blood Pressure and Heart Rate in Unanesthetized and Unrestrained Rats", *Neuropharmacology* 24(5):445-451 (1985).

Okabe, Susumu et al., "Effects of L-Glutamine on Various Gasric Lesions in Rats and Guinea Pigs", *Digestion* 14:325-331 (1976).

Okabe, Susumu et al., "Inhibitory Effect of L-Glutamine on Gastric Irritation and Back Diffusion of Gastric Acid in Response to Aspirin in the Rat", *Digestive Disease* 20(7):626-631 (Jul. 1975).

Okabe, Susumu et al., "Effect of L-Glutamine on Indomethacin-Induced Gastric Lesions in the Rat", *Japan J. Pharmacol.* 24:169-171 (1974).

Pitts, Robert F., "Renal Production and Excretion of Ammonia", *Am. J. Med.* 36:720-742 (May 1964).

Roth, E. et al., "Biochemical Methods for the Determination of a Clinical Protein Catabolism", *Biol. Abstr.* 72(4):Abstr. 25963 (1980).

Roth, E. et al., "Metabolic Responses to Severe Infection and Sepsis", *Biol. Abstr.* 80(11):Abstr. 96352 (1985).

Roth, E., "Changes of the Protein Metabolism in Cachexia and Catabolism", *Biol. Abstr. 80(11):Abstr. 96470 (1985).*

Schmidt, Gerhard M. et al., "Parenteral Nutrition in Bone Marrow Transplant Recipients", *Exp. Hemat.* 8(4):506-511 (Apr. 1980).

Schreck, Robert et al., "Effect of Asparagine and Glutamine Deficiency on Normal and Leukemic Cells", *J. Natl. Cancer Inst.* 51:1103-1107 (1973).

(List continued on next page.)

OTHER PUBLICATIONS

Schwartau, M. et al., "An Experimental Animal Study of Chronic Lack of Thiamin: Alterations in Carbohydrate and Amino-Acid Metabolism at Rest and Under Strain", *Biol. Abstr.* 79(7):Abstr. 61030 (1985).

Schwartau, M. et al., "Tierexperimentelle Studie zum Chronischen Thiaminmangel. Veränderungen des Kohlenhydratund Aminosäurenstoffwechsels unter Ruhe- und Belastungsbedingungen", *Z. Ernaehrungswiss* 23:206-218 (1984).

Smith, Robert J. et al., "Tissue Specific Nutritional Regulation of Glutamine Metabolism", *Clinical Research* 34(2):393A (1986).

Smith, Robert J. et al., "Regulation of Glutamine Metabolism in Cultured Skeletal Muscle Cells", *Diabetes* 31:24A (1982).

Smith, Robert J. et al., "Mechanisms of Selective Alanine and Glutamine Release from Skeletal Muscle", *Diabetes* 33:2A (1984).

Smith, Robert J. et al., "Regulation of Glutamine Synthetase and Glutaminase Activities in Cultured Skeletal Muscle Cells", *J. Cell. Physiol.* 120:197-203 (1984).

Souba, Wiley W. et al., "Gut-Liver Interaction During Accelerated Gluconeogenesis", *Arch Surg* 120:66-70 (Jan. 1985).

Souba, Wiley W. et al., "Intestinal Consumption of Intravenously Administered Fuels", *J. of Parenteral and Enteral Nutrition* 9(1):18-22 (Jan./Feb. 1985).

Souba, Wiley W. et al., "Effects of Glucocorticoids on Glutamine Metabolism in Visceral Organs", *Metabolism* 34(5):450-456 (May 1985).

Souba, Wiley W. et al., "Postoperative Alteration of Arteriovenous Exchange of Amino Acids Across the Gastrointestinal Tract", *Surgery* 94(2):342-350 (Aug. 1983).

Souba, Wiley W. et al., "Glucocorticoids Alter Amino Acid Metabolism in Visceral Organs", *Surgical Forum* 34:74-78 (1983).

Souba, Wiley W., "Glutamine Metabolism in Catabolic States: Role of the Intestinal Tract", *Thesis in Harvard Medical Library* (Jun. 1984).

Stehle, P. et al., "Effect of Parenteral Glutamine Peptide Supplements on Muscle Glutamine Loss and Nitrogen Balance After Major Surgery", *Lancet* ii:231-233 (Feb. 4, 1989).

Szeluga, Debra J. et al., "Nutritional Support of Bone Marrow Transplant Recipients: A Prospective, Randomized Clinical Trial Comparing Total Parenteral Nutrition to an Enteral Feeding Program", *Cancer Research* 47:3309-3316 (Jun. 15, 1987).

Tischler, Marc E. et al., "Leucine Degradation and Release of Glutamine and Alanine by Adipose Tissue", *Biol. Abstr.* 71(3):Abstr. 14875 (1980).

Towne, Jonathan B. et al., "Mechanism of Hyperalimentation in the Suppression of Upper Gastrointestinal Secretions", *Am. J. Surg.* 126:714-716 (Dec. 1973).

Viallard, V. et al., "Effect of Glutamine Deprivation and Glutamate or Ammonium Chloride Addition on Growth Rate, Metabolism and Differentiation of Human Colon Cancer Cell-Line HT29", *Chem. Abstr.* 104:Abstr. 127504p (1986).

Vinnars, Eric et al., "Effect of Parenteral Nutrition on Intracellular Free Amino Acid Concentration", *J. of Parenteral and Enteral Nutrition* 4(2):184-187 (Mar./Apr. 1980).

Weisdorf, Sally A. et al., "Positive Effect of Prophylactic Total Parenteral Nutrition on Long-Term Outcome of Bone Marrow Transplantation", *Transplantation* 43(6):833-838 (1987).

Weisdorf, Sally A. et al., "Total Parenteral Nutrition in Bone Marrow Transplantation: A Clinical Evaluation" *J. of Pediatric Gastroenterology and Nutrition* 3:95-100 (1984).

Wilmore, Douglas W. et al., "The Gut: A Central Organ After Surgical Stress", *Surgery* 104(5):917-923 (Nov. 1988).

Windmueller, Herbert G., "Glutamine Utilization by the Small Intestine", *Adv. Enzymol.* 53:201-237 (1982).

Wolfe, Bruce M. et al., "Substrate Interaction in Intravenous Feeding-Comparative Effects of Carbohydrate and Fat on Amino Acid Utilization in Fasting Man", *Ann. Surg.* 186(4):518-540 (Oct. 1977).

Zanello, M. et al., "Alterations in the Enzyme Profile in Intensive Care Patients Undergoing Total Parenteral Nutrition", *Biol. Abstr.* 70(8):Abstr. 52747 (1980).

Ziegler, Thomas R. et al., "Clinical and Metabolic Efficacy of Glutamine-Supplemented Parenteral Nutrition after Bone Marrow Transplantation", *Ann. Int. Med.* 116(10):821-828 (May 15, 1992).

*Physicians Desk Reference-1972*, pp. 705-707.

*Physicians Desk Reference-1983*, pp. 1418-1421.

*Physicians Desk Reference-1987*, pp. 1419-1422.

Albers, S. et al., "Complete Parenteral Nutrition in Rats With and Without a Synthetic Dipeptide (L-Alanyl-L-Glutamine) With Experimental Catabolism", *Akt. Ernarh.* 9:147-149 (1984) [English translation enclosed].

INTRAVENOUS SOLUTION THAT DIMINISHES BODY PROTEIN LOSS

FIELD OF THE INVENTION

The present invention relates to field of fluid replacement therapy and nutrition. Specifically the present invention provides a novel composition which is capable of diminishing protein loss when administered parenterally or enterally, to a patient.

DESCRIPTION OF THE BACKGROUND ART

The transition from the fed to the fasting state is accompanied by several important metabolic changes. Glucose is the preferred energy source of the brain, red blood cells, and the renal medulla. Muscle and liver stores of glycogen are rapidly depleted and this leaves the fasting individual with two sources of body fuel: protein (primarily from skeletal muscle), and fatty acids (which are deposited in adipose tissue). Despite large triglyceride energy stores, fatty acids cannot be converted into glucose; although the glycerol moiety of triglycerides can be converted into glucose, this supply is quite limited. The only remaining sources of glucose are the gluconeogenic amino acids derived from the breakdown of protein.

Protein is essential to the organism and consists of either functional or structural cellular elements. Protein-containing tissue is referred to as the body cell mass (BCM), and it is this tissue that is active and functional and thus maintains the organism (Moore, F., *The Metabolic Care of the Surgical Patient*, W. B. Saunders Co., Philadelphia, Pa. (1959)). The utilization of protein for endogenous fuel results in a gradual erosion of the BCM, which eventually results in dysfunction. Unfortunately, the energy derived from the oxidation of endogenous fat stores is not sufficient to maintain the BCM. In his classic study of fasting subjects on a life raft in the 1940s, Gamble demonstrated that by providing 100 grams of glucose to the fasting subjects, he could decrease protein loss by 50% (Gamble, J. L., *Harvey Lectures* 42: 247 (1946-1947)). Based on his work, 5% dextrose has become the universal intravenous fluid used in the hospital. Two or three liters of this solution provide 100-150 g dextrose (50 g/L) which reduces net nitrogen breakdown and excretion by one-half.

A variety of studies have been performed in an attempt to further decrease the nitrogen loss in patients who cannot or do not eat. First, it should be noted that Gamble added 40 g protein to the 100 g of carbohydrate and did not observe improvement in nitrogen retention. Others have administered varying amounts of glucose and/or amino acids in a similar attempt to reduce protein loss. The most comprehensive data comes from Moore's Laboratory (Wolff, B. M., et al., *Ann. Surg.* 186: 518 (1977)) and is shown below.

TABLE 1

| Diet | Total Calories kcal/day | Total carbohydrates calories, kcal/day | Nitrogen intake g/m$^2$/day | Nitrogen balance g/m$^2$/day |
|---|---|---|---|---|
| Starvation | 0 | 0 | 0 | −6.44 |
| Low-dose glucose | 568 | 568 | 0 | −4.14 |
| High-dose glucose | 2278 | 2278 | 0 | −3.06 |
| Amino acids | 378 | 0 | 6.8 | −3.22 |
| Amino acids + low-dose glucose | 888 | 540 | 7.4 | −0.68 |

TABLE 1-continued

| Diet | Total Calories kcal/day | Total carbohydrates calories, kcal/day | Nitrogen intake g/m$^2$/day | Nitrogen balance g/m$^2$/day |
|---|---|---|---|---|

As noted from the above table, the administration of calories alone has an effect of reducing negative nitrogen balance. The same is true with the administration of nitrogen; when the two nutrient sources are given together, there is an additive effect which greatly reduces the net negative nitrogen balance.

Glutamine is a nonessential amino acid that is the most abundant amino acid in whole blood and accounts for 60% of the total amino acid pool in skeletal muscle (Bergstrom, J., et al., *J. Appl. Physiol.* 36: 693-696 (1974)). Glutamine has a central role in several metabolic pathways. It contains two nitrogen groups which are readily transferred among tissues, provide a substrate for ammoniagenesis in the kidney, and enhance its role as a precursor for nucleotide synthesis (Marliss, E. B., et al., *J. Clin. Invest.* 50: 814-817 (1971); Pitts, R. F., *Am. J. Med.* 36: 720-742 (1962); Levintow, L., et al., *J. Biol. Chem.* 227: 929-941 (1957)). In addition, glutamine is actively consumed by dividing cells such as lymphocytes and intestinal epithelial cells. During catabolic states, glutamine plasma concentrations may be markedly decreased, intracellular stores may be decreased by 50% while whole plasma levels fall 20-30% (Askanazi, J., et al., *Ann. Surg.* 192: 78 (1980)). This depletion persists long after recovery from the catabolic process (Askanazi, J., et al., *Ann. Surg.* 191: 465 (1980)). Glutamine concentrations in skeletal muscle have been found to correlate well with the rate of protein synthesis (MacLennan, P. A., et al., *FEBS Lett.* 215: 187-191 (1987)) and its administration has been found to inhibit muscle protein breakdown in rats and dogs (MacLennan, P. A., et al., *FEBS Lett.* 237: 133-136 (1988)). This protein loss is not prevented by administering standard total parenteral nutrition (TPN) which is devoid of glutamine (Vinnars, E., et al., *JPEN* 4: 184-187 (1980)). Studies utilizing muscle biopsies in patients undergoing elective surgery have shown that glutamine-supplemented TPN diminished the decline of intracellular glutamine in muscle and counteracted the decrease in protein synthesis (Hammarqvist, F., et al., *Ann. Surg.* 209: 455-461 (1989)).

SUMMARY OF THE INVENTION

The present invention is based on the novel observation that the nitrogen loss a mammal experiences during fluid replacement therapy using intravenously administered 5% dextrose can be significantly decreased by supplementing the intravenous solution with the amino acid glutamine, or a glutamine equivalent, and reducing the amount of dextrose in an isocaloric amount. Based on this observation, the present invention provides novel compositions and methods for reducing nitrogen loss in a mammal when the mammal would normally be administered an intravenous solution of dextrose, for example during rehydration therapy.

DESCRIPTION OF THE PREFERRED EMBODIMENTS

In one embodiment, the present invention provides novel compositions which are capable of reducing nitrogen loss in a mammal in need of rehydration therapy or under conditions which would necessitate the administration of a 5% dextrose solution intravenously. In detail, the compositions of the present invention comprise from about 4% to 10% dextrose and from about ½% to 2% glutamine. The most preferred composition of the present invention consists of 1% glutamine and 4% dextrose. Alternatively, a glutamine equivalent can be substituted for the glutamine in the present composition so long as the glutamine equivalent is capable of being converted to the appropriate amount of glutamine within the mammal.

As used herein, a "glutamine equivalent" is defined as an analogue, substitution product, isomer, homologue, metabolite, or derivative of glutamine which can donate an amine group and be metabolized in the Krebs cycle. Most preferred are compounds which process at least one glutamine residue such as small polypeptides or dipeptide containing glutamine.

As used herein, the term "mammal" is intended to include, but not be limited to, humans, pigs, cattle, cats, dogs and rodents.

As used herein, the term "reducing nitrogen loss" is defined as any decrease in the net amount of nitrogen loss by the body when compared to the level of nitrogen loss observed with starvation, i.e., no rehydration therapy. For example, it has been previously shown that a 50% reduction in nitrogen (protein) loss during rehydration therapy can be achieved by administering to the mammal an appropriate amount (approximately 2 liters for a human subject) of 5% dextrose. The present invention discloses that this net loss can be decreased to approximately 25% when the solution which is administered consists of from about 4% dextrose and from about 1% glutamine.

A mammal is said to be suffering from protein loss when the net nitrogen balance of the mammal decreases ore becomes negative over a specific period of time. A variety of tests can be employed to determine if a mammal is suffering from nitrogen loss. However, in general, protein loss is measured by comparing the amount of nitrogen administered to the mammal with the amount of nitrogen excreted from the mammalian urine.

The compositions of the present invention may be administered by any means so long as the composition achieves the intended purpose of reducing net nitrogen loss. In a preferred embodiment, the compositions of the present invention are administered parenterally; more preferably intravenously. The preferred route of administration is intravenous administration. However enteral, i.e. oral, administration can be employed as well. The amount and the regime used for the administration of the compositions of the present invention can be readily determined by those with ordinary skill in the art.

The compositions of the present invention can be formulated so as to be administered by any means or routes so long as the composition achieves the intended purpose of reducing nitrogen loss during rehydration. Further, the amount and regimes employed for the administration of glutamine, or a glutamine equivalent in a dextrose solution can be readily determined by those with ordinary skill in the art.

As used herein "parenteral" is defined as that region outside the digestive tract.

As used herein, "enteral" is defined as that portion of the alimentary canal including the stomach and the portion distal to the stomach.

The amount of glutamine or glutamine equivalent and the frequency of administration will vary depending upon the needs of the mammal. For a mammal suffering from dehydration, it is preferable to administer the compositions of the present invention continuously or at frequent intervals throughout the day. Depending upon the severity of the dehydration and the complications associated therewith, it is generally preferred that the compositions of the present invention be administered intravenously.

Enteral administration can be accomplished by tubing placed via the nose into the gastric or duodenal regions whereas parenteral administration include, but are not limited to, routes such as subcutaneous, intramuscular, or intravenous injection. Preparations for parenteral administration include sterile aqueous or non-aqueous solutions, suspensions and emulsions.

In another embodiment, the present invention provides methods of reducing nitrogen loss in a mammal when the mammal would normally be administered an intravenous solution of dextrose, such as a means of alleviating dehydration which is associated with post-operative trauma or with pathological infection such as cholera.

In detail, a mammal fed solely with an intravenous solution of 5% dextrose can be expected to have a net nitrogen loss of approximately 50% of the loss which would be observed without the administration of the dextrose solution. As stated above, when the compositions of the present invention (4% dextrose and 1% glutamine) are administered to the mammal, the net nitrogen loss will be reduced to approximately 25% of that observed without the administration of an intravenous solution.

The methods of the present invention and compositions employed for reducing nitrogen loss can be used to decrease the nitrogen loss and dehydration associated with any state or pathological condition in which dehydration and nitrogen loss occurs or where there has been recognized in the past a need to administer an intravenous solution of 5% dextrose. These include, but are not limited to post-operative trauma, bacterial infection such as cholera, and various malabsorption syndromes of the gut. In the preferred embodiment, the present methods and compositions are employed to decrease the nitrogen loss and dehydration which is associated with post-operative intravenous rehydration therapy.

The methods of the present invention are used to reduce the dehydration and nitrogen loss which is associated with condition which mimic starvation. Since the methods and compositions of the present invention are directed to the dehydration and nitrogen loss which is present, and not to the condition itself, the methods and compositions can be utilized to treat all conditions which resulting in nitrogen loss and dehydration. An illustration of this is the use of the methods and compositions of the present invention in treating the dehydration and nitrogen loss which is associated with surgical operations.

Having now generally described the invention, the methods and agents will be more readily understood through reference to the following examples. These examples are provided by way of illustration and are not intended to limit the present invention unless specified otherwise.

EXAMPLE 1

All of the previous studies that have been performed have used amino acid solutions devoid of glutamine. In an effort to determine the effect of this amino acid when added to standard peripheral intravenous solutions, we have studied 10 healthy male volunteers who were randomized to receive isocaloric infusions of either 5% dextrose (standard hospital treatment) or 4% dextrose plus 1% glutamine during a 5-day fast. All subjects received 1400 ml solution/m² body surface area. Electrolytes were standardized and were also added to all solutions. The patients were weighed daily and all urine was collected.

TABLE 2

|  | N Balance g/m²/day | % Change in Body Weight | Sodium balance g/m²/day |
|---|---|---|---|
| 5% Dextrose | −4.20 | −2.62 | +1.5 |
| 4% Dextrose + 1% glutamine | −2.75* | −1.89 | +18.1* |

*p < 0.05 vs dextrose, by convention (−) means loss, (+) means gain.

GLN supplementation improved nitrogen balance by 35% relative to volunteers receiving dextrose alone. Losses in body weight also were decreased in the GLN group. GLN volunteers had a 12-fold increase in sodium balance, when compared to the volunteers receiving dextrose alone. This study demonstrates that the addition of GLN to peripheral IV fluids improves nitrogen balance compared to standard therapy of 5% dextrose. The single administration of dextrose with one amino acid is more efficient than administering a large quantity of amino acids (see Table 1, amino acids alone). This solution approaches the nitrogen sparing effects observed with solutions of amino acids and low-dose glucose, although the quantity of calories and nitrogen is much less. The 4% dextrose plus 1% glutamine solution provides only 380 glucose calories/day, and only 2.24 g nitrogen/m²/day. Thus, this solution represents a much more efficient mixture to enhance nitrogen sparing than previously realized.

What is claimed is:

1. A composition for decreasing dehydration and nitrogen loss in a mammal comprising from about 4% to 10% dextrose and from about ½% to 2% glutamine, or glutamine equivalent, wherein said glutamine equivalent is capable of being converted to glutamine by said mammal.

2. The composition of claim 1 wherein said composition comprises 4% dextrose and 1% glutamine.

3. The composition of claim 2 wherein said composition consists essentially of 4% dextrose and 1% glutamine.

4. A method of reducing dehydration and nitrogen loss in a mammal comprising the step of administering to said mammal an effective amount of a composition capable of reducing dehydration and nitrogen loss wherein said composition comprising from about 4% to 10% dextrose and from about ½% to 2% glutamine, or glutamine equivalent, wherein said glutamine equivalent is capable of being converted to glutamine by said mammal.

5. The method of claim 4 wherein said composition comprises 4% dextrose and 1% glutamine.

6. The method of claim 5 wherein said composition consists essentially of 4% dextrose and 1% glutamine.

* * * * *